United States Patent
Do et al.

(10) Patent No.: US 6,452,677 B1
(45) Date of Patent: Sep. 17, 2002

(54) METHOD AND APPARATUS FOR DETECTING DEFECTS IN THE MANUFACTURE OF AN ELECTRONIC DEVICE

(75) Inventors: Douglas Do; Ted Taylor, both of Boise, ID (US)

(73) Assignee: Micron Technology Inc., Boise, ID (US)

( * ) Notice: Subject to any disclaimer, the term of this patent is extended or adjusted under 35 U.S.C. 154(b) by 0 days.

(21) Appl. No.: 09/023,925

(22) Filed: Feb. 13, 1998

(51) Int. Cl.[7] .............................................. G01B 11/00
(52) U.S. Cl. ................. 356/394; 356/237.3; 356/237.4; 356/388; 250/307; 250/310
(58) Field of Search ................................. 356/372, 373, 356/388, 390, 394, 237.1–4; 250/310, 307, 201.3; 324/751; 382/170, 286

(56) References Cited

U.S. PATENT DOCUMENTS

| | | | |
|---|---|---|---|
| 4,556,317 A | | 12/1985 | Sandland et al. |
| 4,794,646 A | * | 12/1988 | Takeuchi et al. ............. 250/310 |
| 5,057,689 A | | 10/1991 | Nomura et al. |
| 5,109,430 A | | 4/1992 | Nishihara et al. |
| 5,555,319 A | * | 9/1996 | Tsubusaki et al. .......... 382/170 |
| 5,641,960 A | | 6/1997 | Okubo et al. |
| 5,659,172 A | | 8/1997 | Wagner et al. |
| 5,750,990 A | * | 5/1998 | Mizuno et al. ............. 250/307 |
| 5,757,198 A | * | 5/1998 | Shida et al. ................ 324/751 |
| 5,777,327 A | * | 7/1998 | Mizuno ....................... 250/310 |
| 5,986,263 A | * | 11/1999 | Hiroi et al. .................. 250/310 |
| 6,067,153 A | * | 5/2000 | Mizuno ....................... 356/237 |
| 6,114,681 A | * | 9/2000 | Komatsu .................. 250/201.3 |
| 6,157,451 A | * | 12/2000 | Mizuno ....................... 356/394 |

OTHER PUBLICATIONS

Silicon Processing for the VLSI ERA, vol. 1, Stanley Wolf, et al, p. 489, 1986.

* cited by examiner

Primary Examiner—Frank G. Font
Assistant Examiner—Sang H. Nguyen
(74) Attorney, Agent, or Firm—Dickstein Shapiro Morin & Oshinsky LLP (57) ABSTRACT

The invention provides a unique method and apparatus for detecting defects in an electronic device. In one preferred embodiment, the electronic device is a semiconductor integrated circuit (IC), particularly one of a plurality of IC dies fabricated on a wafer of silicon or other semiconductor material. The defect detection operation is effectuated by a unique combination of critical dimension measurement and pattern defect inspection techniques. During the initial scan of the surface of the wafer, in an attempt to locate the appropriate area for a critical dimension (CD) feature or element that is to be measured, a "best fit" comparison is made between a reference image and scanned images. The critical dimension measurements are conducted on a "best fit" image. In addition, a "worst fit" comparison is made between the reference and scanned images. A "worst fit" determination represents pattern distortions or defects in the ICs under evaluation.

48 Claims, 9 Drawing Sheets

METHOD AND APPARATUS FOR DETECTING DEFECTS IN THE MANUFACTURE OF AN ELECTRONIC DEVICE

BACKGROUND OF THE INVENTION

1. Field of the Invention

The invention is directed to the field of fabricating and manufacturing electronic devices. More specifically, the invention is directed to a measurement and detection method and apparatus for detecting defects in the manufacture of an electronic device such as a semiconductor integrated circuit or a wafer composed of a plurality of integrated circuits.

2. Description of Related Art

In the semiconductor industry, there is a continuing movement towards higher integration, density and production yield, all without sacrificing throughput or processing speed. The making of today's integrated circuits (ICs) requires a complex series of fabrication, inspection and testing steps interweaved throughout the entire process to ensure the proper balance between throughput, processing speed and yield. The inspections and tests are designed to detect unwanted variations in the wafers produced, as well as in the equipment and masks used in the fabrication processes. One small defect in either the devices produced or the process itself can render a finished device inoperable.

Many of the inspection steps once done manually by skilled operators have been automated. Automated systems increase the process efficiency and reliability as the machines performing the inspection are more consistent than human operators who vary in ability and experience and are subject to fatigue when performing repetitive tasks. The automated systems also provide greater amounts of data regarding the production and equipment, which enables process engineers to both better analyze and control the process.

Figure 1:
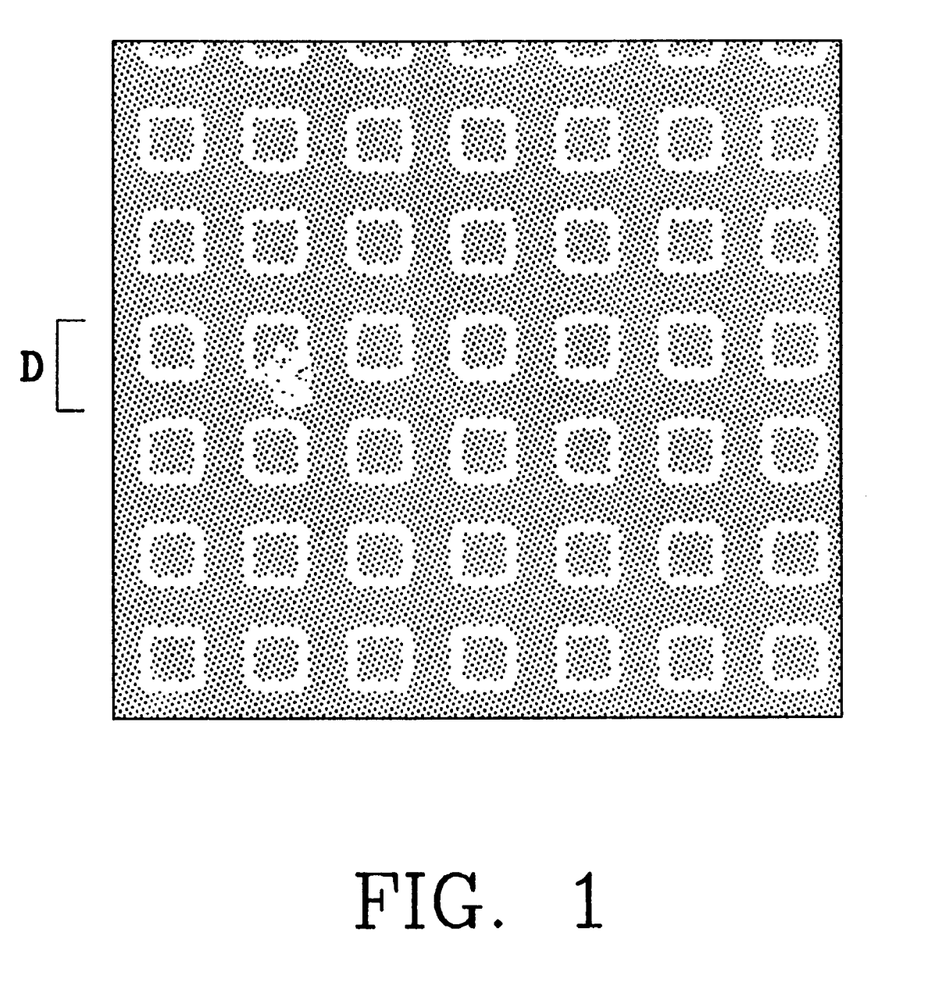
FIG. 1 illustrates patterns of integrated circuit dies formed on a silicon wafer.

One such automated inspection step is known as "pattern inspection." Many different "patterns" appear on both the wafer and the masks used to produce the ICs. Patterns may be repeated areas on a single IC such as test areas, memory areas, shift registers, adders, etc., or, as shown in FIG. 1, the ICs (or dies) themselves may be considered a "pattern" that is repeated throughout the wafer.

Typical pattern inspection systems are image based, as described, for example, in U.S. Pat. Nos. 4,794,646; 5,057,689; 5,641,960; and 5,659,172. In U.S. Pat. No. 4,794,646, for example, the wafer, or part thereof, is scanned and a highly resolved picture or image of the pertinent "pattern" is obtained. This pattern image is compared to other pattern images retrieved from the same or other wafers, or is compared to an ideal image stored in the inspection system database. Differences highlighted in this comparison identify possible defects in the IC or wafer.

Another inspection step that is typically automated in processes today is known as "critical dimension (CD) measurement." On each integration level there is a region or set of patterns or features whose dimensions are critical to the functioning of the entire circuit. A representative pattern is chosen for CD measurements. Examples of CD features include transistor channel length (gate length), transistor channel width, trench depth, step slope, spacing, contact dimensions, etc. Like pattern inspection, CD measurement can be done during several different stages in the fabrication process (e.g., masking, developing, final inspection, etc.).

With the increase in integration, the dimensions to be measured as CDs are so minute that scanning electron microscopes (SEMs) have replaced other optical systems as the tool for performing CD measurements. See, e.g., U.S. Pat. No. 5,109,430. Indeed, SEMs made exclusively for CD measurements are commonplace.

The ability of a viewing system to distinguish detail is related to the wavelength of the light (radiation) used. The shorter the wavelength, the smaller the detail that can be seen. With feature sizes breaking the sub-micron barrier, it is imperative that variations in the lower sub-micron range be detected. One error, even of this small magnitude, may be enough to render the entire IC or wafer useless. Only the SEM provides the capability to detect these variations.

For automated CD-SEMs, fiducial markers on wafers are typically included for the purpose of locating certain features or structures—usually test targets. U.S. Pat. No. 5,109,430, for example, discloses use of fine scale marks fabricated in a pattern in a two-dimensional array to form a target occupying a region of the IC where circuitry is not to be formed, e.g., between bonding pads or in a region interior to the bonding pads. Different patterns on different layers can be used to detect misalignment between layers, as well as measure critical dimensions of the patterns.

These "test targets" are specially designed structures included on the wafer for test purposes only. If the test targets are the correct size and shape, it follows that other semiconductor devices in their proximity will also have the correct size and shape and will therefore function properly. During its scanning of the wafer surface, the CD-SEM compares stored image data of the fiducial wafer markers with the scanned images received from the current position of the wafer under the CD-SEM. Once a "best match" is made, the CD-SEM is in correct position to perform the CD measurement on the intended "test target" for that particular location of the wafer (or IC).

With each new level of integration achieved, a number of new fabrication steps are introduced. This increase is inherently followed by a similar increase in the inspection and testing steps needed to ensure quality control of the products. The increased complexity of the process, however, typically leads to a reduction in throughput or processing speed.

SUMMARY OF THE INVENTION

The invention provides a unique apparatus for and method of detecting defects in an electronic device. In one preferred embodiment, the electronic device is a semiconductor integrated circuit (IC), particularly one of a plurality of IC dies fabricated on a wafer of silicon or other semiconductor material. The defect detection operation is effectuated by a unique combination of critical dimension measurement and pattern inspection techniques. During the initial scan of the surface of the wafer, in an attempt to locate the appropriate critical dimension (CD) feature or element that is to be measured during a CD measurement procedure, a "best fit" comparison is made between a reference feature image and the currently scanned feature image. In addition, a "worst fit" comparison is made between the reference feature image and the scanned feature images. A "worst fit" determination represents pattern distortions or defects in the ICs under evaluation.

The invention thus provides a method and apparatus for detecting defects in an electronic device while scanning for the areas at which critical dimension measurements are to be made, thereby avoiding the need to carry out the otherwise separate steps of defect pattern recognition and CD measurement.

BRIEF DESCRIPTION OF THE DRAWINGS

The foregoing and other features and advantages of the invention will become more apparent from the detailed description of the preferred embodiments of the invention given below with reference to the accompanying drawings in which.

DETAILED DESCRIPTION OF PREFERRED EMBODIMENTS

The present invention will be described in detail with reference to preferred embodiments illustrated in the accompanying drawing figures. Although these embodiments depict the invention as in its preferred application to a semiconductor device formed in a silicon wafer, it should be readily apparent that the invention has equal application to any type or configuration of semiconductor device (e.g., microprocessor, microcomputer, memory circuit, digital signal processor (DSP), programmable logic array (PLA), etc.) in any type of arrangement (e.g., individual die, packaged die, etc.), as well as any other electronic device (e.g., flat panel displays, liquid crystal displays (LCDs), etc.) that encounters the same or similar problems.

Figure 2:
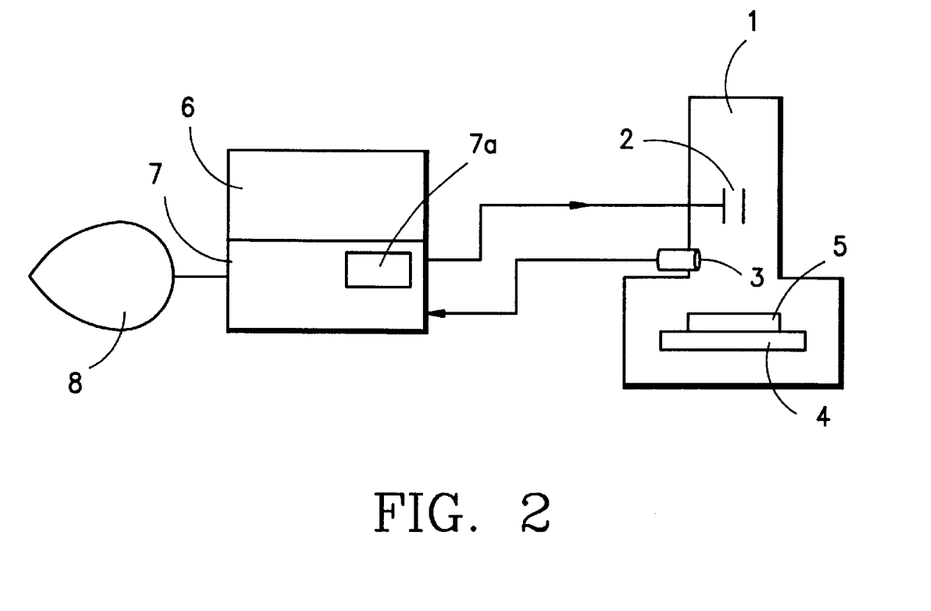
FIG. 2 is a schematic diagram of a SEM in accordance with a preferred embodiment of the invention.

In accordance with a preferred embodiment of the invention, a method and apparatus for detecting defects in the manufacture of an electronic device such as an integrated circuit (IC) on a silicon wafer is provided. In one implementation, a defect detection station, as shown in FIG. 2, can be constructed having a scanning electron-beam microscope (SEM) 1 used for viewing purposes, as is well known in the art. Although the invention is described herein as used during final wafer inspection of the IC dies, it can readily be appreciated that the invention has application to any other stage of manufacturing, e.g., inspection after the initial photomasking and baking of a wafer known as "development inspection," where critical dimension measurements or pattern inspections are contemplated.

SEM 1 is provided with an object support structure 4 in the form of a stage or chuck, which may be moveable or stationary. An object 5 under evaluation such as an IC sample die or a wafer containing many IC dies rests on stage 4. Under control of computer 6, the stage 4 may be moveable in two (X-Y) or three (X-Y-Z) dimensions to facilitate the proper viewing of object 5 (or parts thereof). A deflector 2 and detector 3, whose operations will be described in detail below, are also provided within SEM 1 to assist in the viewing of object 5. An image processor 7, together with its accompanying Image memory 7a are provided to process the image signals output by SEM 1 and transform the signals into visual representations or data which can be viewed on a display monitor 8 (e.g., cathode ray tube (CRT)) or used for processing in computer 6.

In operation, SEM 1 uses a finely focused electron beam directed by deflector 2, preferably under the control of computer 6, to scan the surface of the object 5 resting on stage 4, typically in two dimensions (X-Y). For the purposes of discussion only, it will be assumed herein that the object 5 under evaluation is a silicon wafer having a plurality of semiconductor integrated circuit dies fabricated thereon. The electrons striking the semiconductor surface of object 5 collide with inner shell electrons of the object atoms causing inelastic collisions of low energy emitting so-called "secondary electrons" which are serially detected by detector 3.

The detected electron current is output as an image signal to computer 6 and image processor 7 where an image representative of the surface of the object 5 can be formed based on the image signal. This image is stored in image memory 7a and can be viewed on monitor 8 or otherwise processed by computer 6. The high resolution of the image is attributed to the small diameter (e.g., several nanometers) of the electron beam illuminator. The visual contrast achieved in the image originates mostly from variations in the extent of the secondary electron emissions from the topographic features of the surface of the object 5.

Figure 6A:
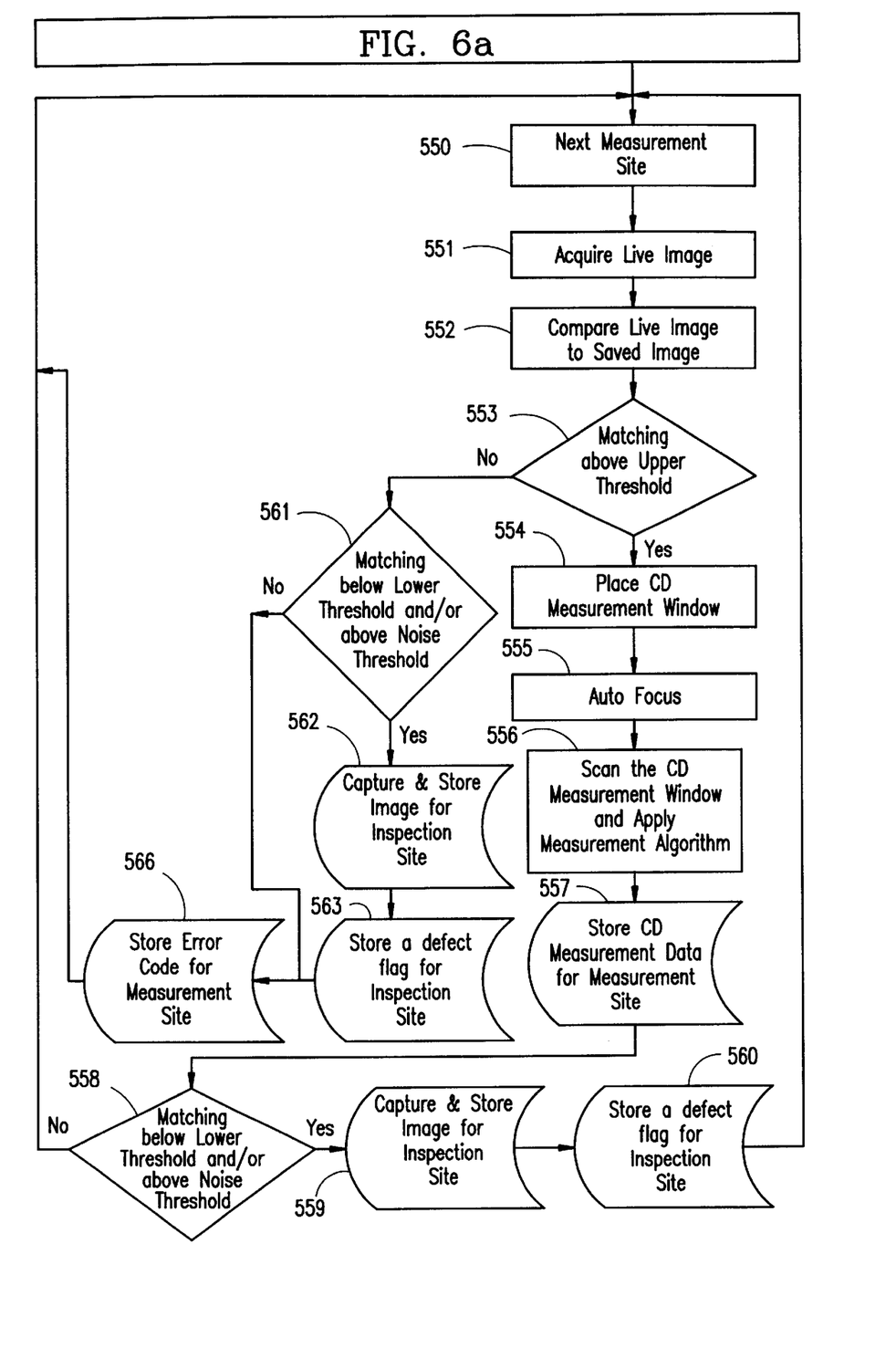
FIGS. 6a and 6b are flowcharts describing the operation of yet additional preferred embodiments of the invention.
Figure 6B:
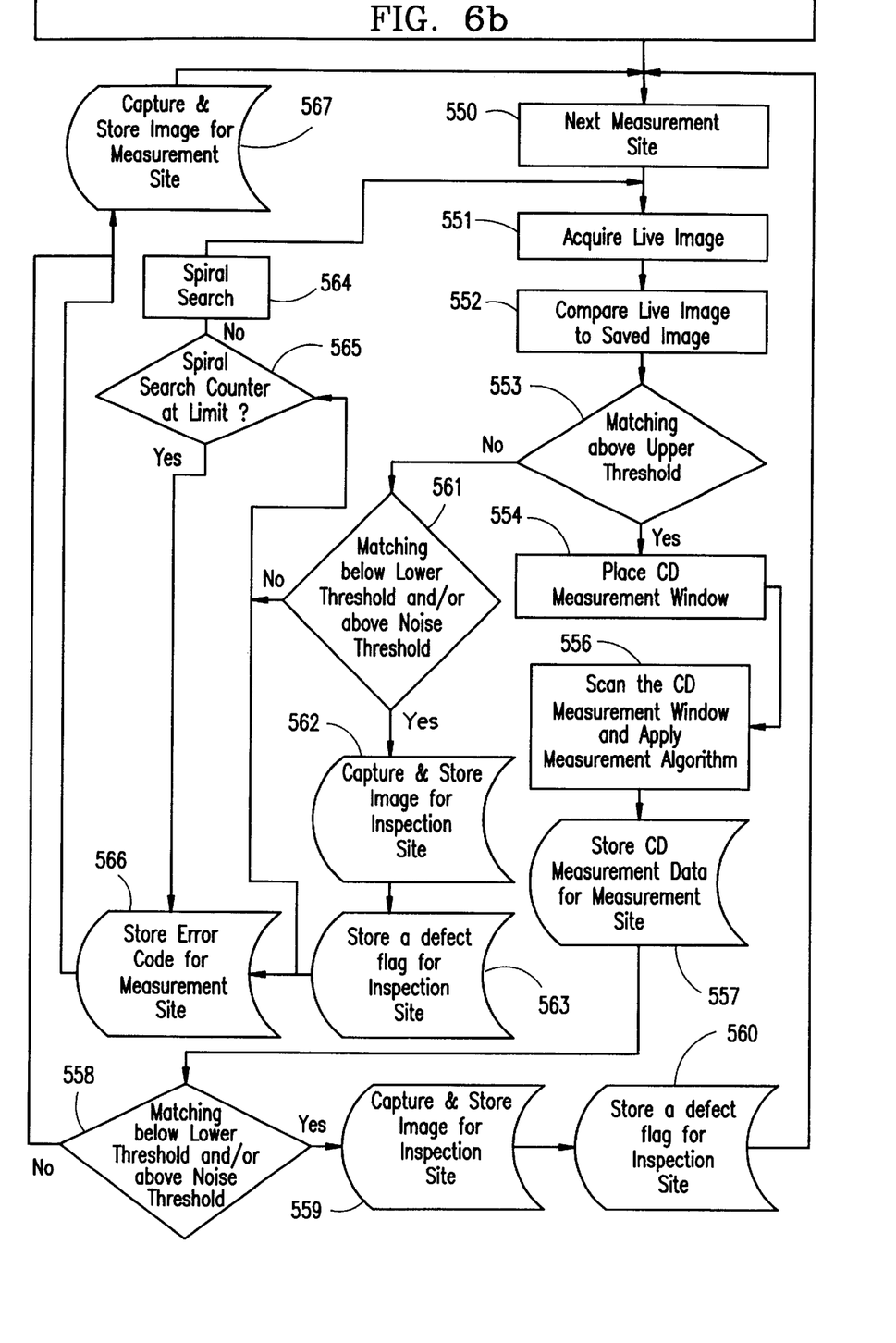
Figure 7:
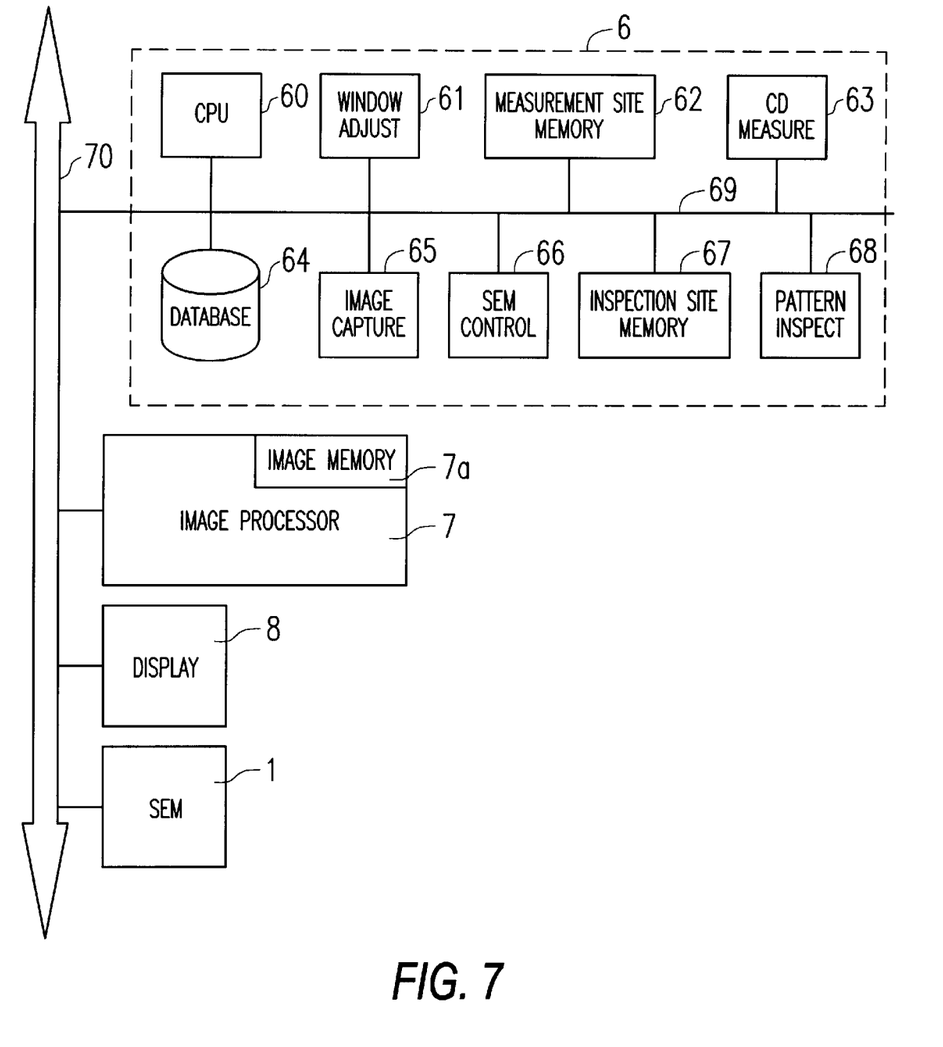
FIG. 7 is a block diagram of an apparatus in accordance with an preferred embodiment of the invention.

As shown in FIG. 7, the defect detection station (FIG. 2), in accordance with one preferred embodiment of the invention, incorporates within computer 6 a collection of modules such as central processing unit 60, a window adjust unit 61, a measurement site memory 62, a CD measurement unit 63, a database 64, an image capture unit 65, a SEM control unit 66, an inspection site memory 67, a pattern inspect unit 68, and local bus 69. These modules may either be hardware components, software components, or a combination of hardware/software components constructed as known in the art to accomplish the functions described herein. The components may be implemented individually or together as a single group (e.g., a single computer program run on a computer processor or the like such as CPU 60). Indeed, in one example, the invention may be implemented in a conventional CD-SEM such as the "IVS-200" made by IVS, Inc., the "Opal 7830si" made by Applied Materials, or the "S-8820/8620" made by Hitachi, by modifying the computer program used by the control computer within the SEM such that the control computer implements in software the functions of each module described herein and the operations performed in the flowcharts of FIGS. 4a through 6b. Individual ones of the, components may also be combined into smaller groups, e.g., CD measure 63 and pattern inspect 68 may be combined with CPU 60, while-measure site memory 62 and inspection site merry 67 can be combined. These modules in computer 6, together with SEM 1, image processor 7, image memory 7a, and display 8 are operatively connected to one another to facilitate the operation of various preferred embodiments of the invention, as will be described below.

In detecting defects in the object 5, the invention relies on a combination.of pattern inspection and critical dimension measurement techniques. In particular, the invention relied on the use of a SEM, which performs critical dimension measurements, to perform the pattern inspection while the SEM is performing its function of CD measurement. As the SEM is searching for the "best match" image of a fiducial wafer marker, the SEM simultaneously searches for differences between stored reference patterns and the image patterns detected from the current wafer. Where the SEM detects a significant aberration in the current image pattern, as shown as pattern 44b in FIG. 3 (as well as in region "D" on FIG. 1), the SEM determines that a defect has been found. As an alternative to the fiducial wafer markers, other CD features or other components of an IC or wafer may be used for measurement such as transistor channel length (gate length), transistor channel width, trench depth, step slope, spacing, contact dimensions, etc.

Figure 3:
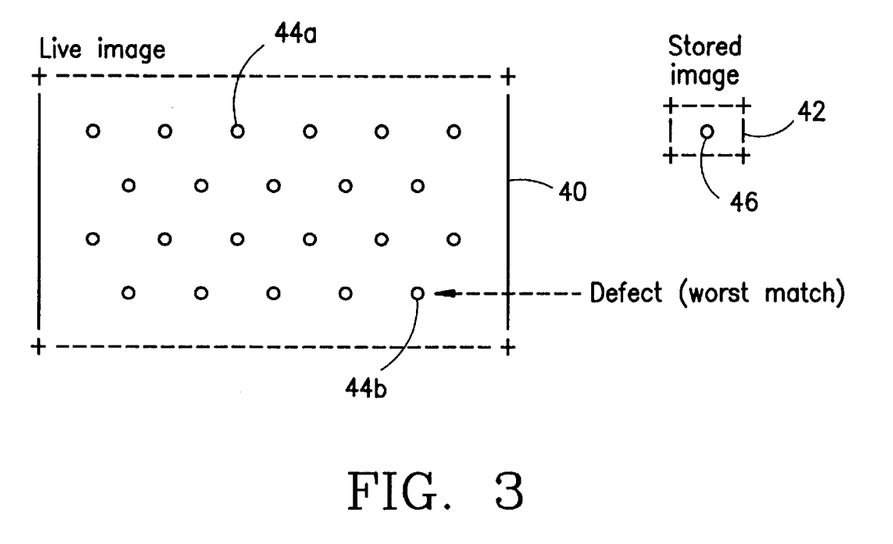
FIG. 3 shows images captured by a SEM in accordance with a preferred embodiment of the invention.

The foregoing operation is more fully described with reference to the flowcharts in FIGS. 4a, 4b, 5a, 5b, 6a and 6b, which are executed, for example, by the SEM computer and with each representing a respective preferred embodiment of the invention. In the first of these embodiments, depicted in FIG. 4a, SEM control 66 (FIG. 7) controls the deflector 2 and stage 4 to permit SEM 1 to scan one or more measurement sites of the wafer 5 (S10). The measurement site is preferably one of several different regions or sections of an IC die fabricated on the wafer 5 (although it may also be one of several sections of wafer 5 made up of a plurality of IC dies). As shown in FIG. 3, each measurement site 40 preferably contains a plurality of cells 44a, 44b in a semiconductor memory device. The sites may alternatively contain a plurality of circuit components or features of the IC, or they may even be a plurality of IC dies. In an alternative embodiment, "test target" regions may serve as measurement sites. "Test targets" are made up of non-functional structures that are fabricated in portions of the wafer or IC itself where no functional circuitry is placed, as described in U.S. Pat. No. 5,109,430, which is incorporated herein by reference in its entirety.

SEM 1 then initiates acquisition or capture (S11) of a "live" image of the image area. For purposes of illustration only, we assume that the "live" image is over a plurality of cells, e.g., 44a, 44b, etc. in a semiconductor memory, as shown in FIG. 3. To achieve this image capture, computer 1 relies on detector 3 to sense the secondary electrons emitted from the area on wafer 5. Image capture module 65 takes control of the transmission of the image signal output from detector 3 to image processor 7, as well as the storage of the "live" image, as represented by the image signal, in image memory 7a.

Central processing unit (CPU) 60 then retrieves a stored image 42 (FIG. 3) of a pattern or feature 42 that serves as the reference (or "ideal") pattern that can be used as a template. In the preferred embodiment, the reference pattern is an image of a semiconductor memory cell created based on design rules, etc. developed by manufacturing personnel and stored in database 64 (or some other storage device). The image 42 may also be taken from a calibrating "reference" wafer, from other in-line wafers, or even from adjacent IC dies or measurement sites on the same wafer 5, as can be recognized by those of ordinary skill in the art.

CPU 60 then performs in Step S12 a comparison between all of the cells, including cells 44a and 44b, of the measurement site 40 and the reference cell 46 of stored image 42 to determine the similarities (or dissimilarities) between the individual measurement site cells such as 44a and 44b, and reference cell 46, and to produce a comparison score reflecting the similarities/dissimilarities. Any known comparison algorithm or calculating device may be utilized to produce a comparison score that provides some indication of similarities/dissimilarities of the images. For example, CPU 60 may be programmed to calculate an image quotient by dividing the number of pixels found to be the same between the live and reference sites by the total number of pixels available. CPU 60 uses the comparison score thus calculated to determine the "best fit" between each of the "live" measurement cell sites and the stored measurement site 46.

Figure 4A:
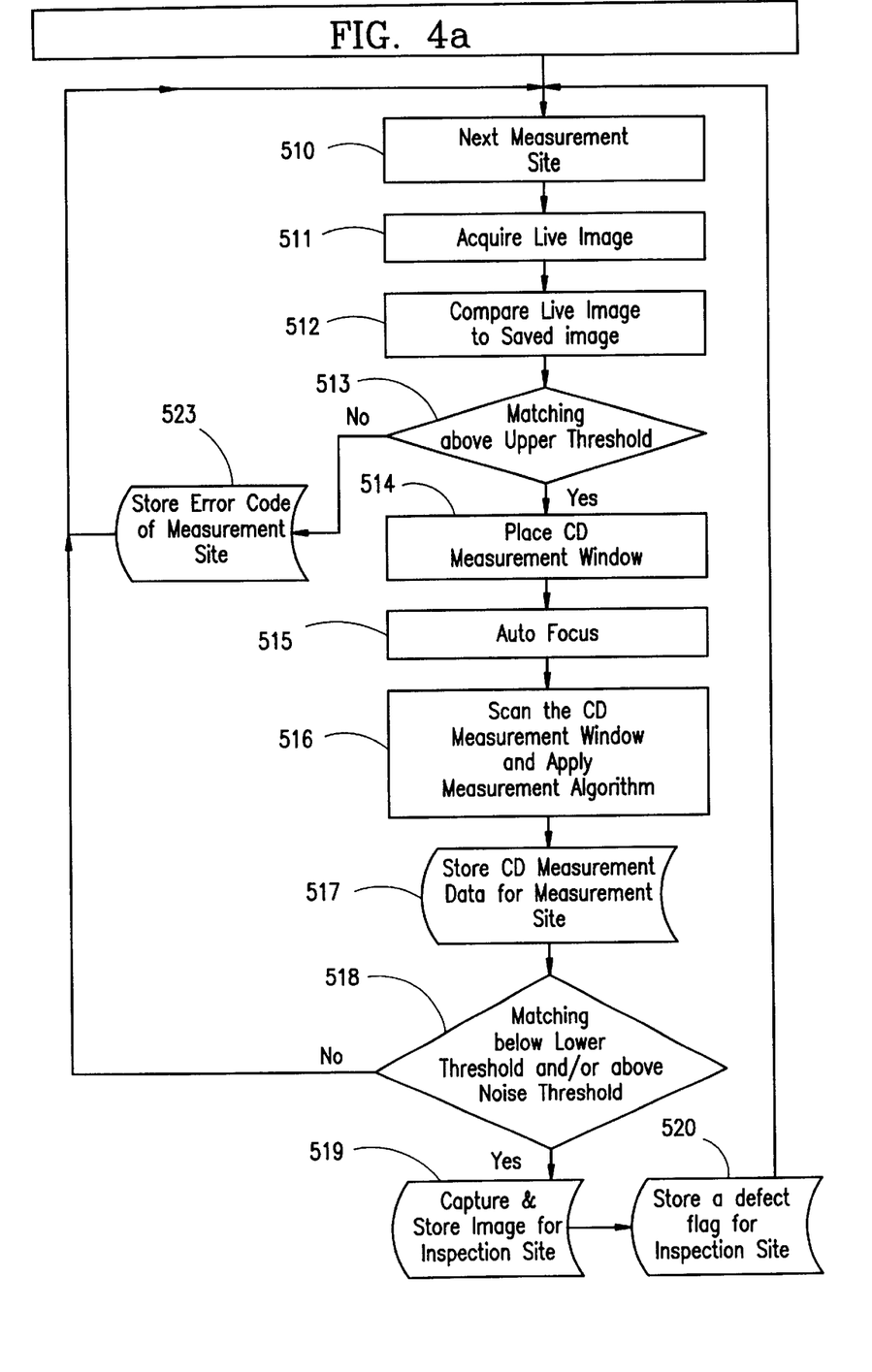
FIGS. 4a and 4b are flowcharts describing the operation of preferred embodiments of the invention.

The "best fit" may be found by determining whether any the comparison scores for an individual measurement site under evaluation exceeds an upper threshold (S13). In particular, the "best fit" may be found by determining whether the comparison score for an individual measurement site cell, e.g., 44a, under evaluation exceeds an "upper threshold" value, which is preferably assigned by the operator, engineer, or designer and stored in the database 64 or other program memory prior to use on the manufacturing floor. (S13).

In the preferred embodiment, during step S12, CPU 60 will compare the image of an individual cell of measurement site 40 with the reference cell 46 of reference site 42 stored in database 64. For each individual cell considered, CPU 60 will calculate a comparison score until CPU 60 detects a comparison score that exceeds the "upper threshold" value. The first time the "upper threshold" is exceeded based on one of the cells, e.g., 44a, 44b, CPU 60 will send an enable signal over local bus 69 to CD measure unit 63, which is operative to perform a CD measurement on the feature or structure appearing at the current measurement site cell 44a (S13). If CPU 60 has compared all of the cells in measurement site 40 to the reference cell 46 and found that none of the calculated comparison scores exceed the "upper threshold" value (S13), the process turns to step S23, which will be described later below.

Where the "upper threshold" value has been exceeded by a cell site, however, a CD measurement procedure begins in step S14. To accomplish the CD measurement, window adjust module 61 places a CD measurement window around the current measurement site, e.g. 44a (S14). Preferably, SEM control 66 directs stage 4 to reposition wafer 5 and automatically focus (S15) SEM 1 to permit CD measurements to be made, in a manner well known in the art. Using image capture module 65, together with image processor 7 and image memory 7a, the surface of the wafer 5 within the CD measurement window is scanned into image memory 7a, and the CD measurements taken by CD measure unit 63 (S16). CD measure unit 63 may employ any CD measurement algorithm or technique known in the art to produce the dimensions or sizes of the measurement feature. U.S. Pat. No. 5,555,319, for example, which is incorporated by reference herein in its entirety, illustrates one such CD measurement technique that may be utilized in CD measurement unit 63. The CD measurement data derived is then stored in measurement site memory 62 (S17).

After the CD measurements are taken, CPU 60 next determines whether any of the above-calculated comparison scores falls below a "lower threshold" (S18). During the comparison score calculations in step S12, CPU 60 stores in an internal/external CPU memory (not shown), database 64, or any other storage unit, the calculated comparison scores for each cell of the measurement site 40 being evaluated. In step S18, CPU 60 reviews the stored comparison scores and determines which, if any, fall below the "lower threshold" value. In the case where comparison scores for all of the cells 44a, 44b were not calculated in step S12 because a cell was reached which exceeded the upper threshold in step S13, CPU 60 proceeds to calculate the remainder of the comparison scores for the remainder of cells in measurement site 40.

As with the "upper threshold," value, the value assigned to the "lower threshold" is preferably predetermined prior to use on the manufacturing floor. Where CPU 60 finds that any of the comparison scores falls below the "lower threshold," CPU 60 directs image capture module 65 to capture the current "live" image 40 or, alternatively, only the image of the defective cell 44b, and store the image in inspection site memory 67 (S19). Subsequently, CPU 60 stores a defect flag corresponding to the defect detected in inspection site memory 67 (S20). CPU 60 then causes the basic process flow to repeat for the next measurement site 40 (S10).

In the event, in step S18, CPU 60 finds that none of the comparison scores fall below the "lower threshold" value for any of cells 44a, 44b, CPU 60 restarts the process again with the next measurement site (S10).

Where CPU 60, in step S13, finds that none of the comparison scores exceed the "upper threshold" value, CPU 60 may cause an "error code" to be stored in measurement site memory 62 (S23) associated with the measurement site 40 under evaluation. The process may then begin again with the next measurement site (S10).

In an alternative embodiment, the "upper threshold" (described above) may be dynamically assigned based on the relative comparison scores of other measurement site cells in the same live image 40, or based on other live images on the same wafer, or based on completely different wafers. For example, CPU 60 may scan and calculate comparison scores for all the measurement site cells in one particular live image 40. The CPU 60 would then assign as the "upper threshold" value a number just below the comparison score that represents the highest similarity between live image measurement site cell, e.g., 44a, 44b, and reference site cell 46. The CPU 60 would then locate the measurement site that exceeds this threshold, as in step S13.

Alternative embodiments may also rely on a "noise threshold" value to provide additional checks on the quality of the device produced or the process itself. Often stray or spurious noise signals attributed to operation of the SEM or the environment surrounding the SEM cause imperfections to appear in the scanned image even though there are no imperfections in the underlying device under inspection. These noise signals must be distinguished from the distortions or defects actually present in the patterns found on the electronic device. By assuming that a small portion of the comparison score will be affected by the noise level, and taking this noise level into account when determining whether a defect exists, the effects of the noise on the detection system can be diminished. Thus, step S18, for example, may be modified to require that the comparison score be above the "noise threshold" as an added condition, as shown in FIGS. 4a and 4b.

As another alternative, in step S18, should CPU 60 determine that a calculated comparison score falls below the "lower threshold" value, CPU 60 will send an enable signal via local bus 69 to pattern inspect unit 68 to initiate a pattern inspection procedure using any of the known inspection algorithms or techniques in the art. U.S. Pat. No. 4,556,317, for example, which is incorporated by reference herein in its entirety, illustrates one such pattern inspection technique that may be utilized in pattern inspect unit 68. After conducting the procedure, should pattern inspect unit 68 then determine the presence of a pattern distortion or defect, the "defect flag" step (S20) can then be performed, as described above.

Figure 4B:
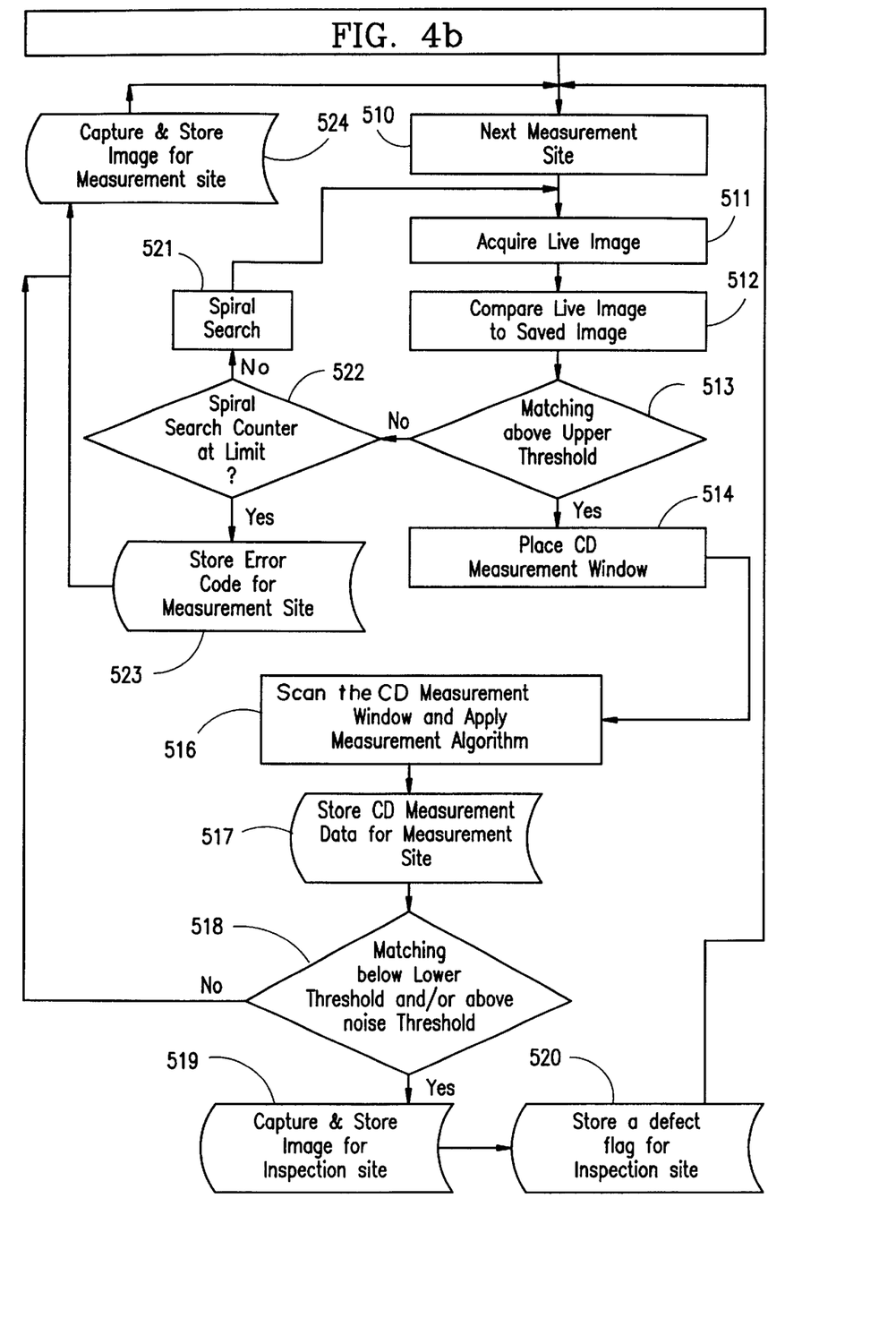

FIG. 4b illustrates another embodiment of the invention. Many of the steps shown in FIG. 4a, as described above, are retained and bear the same reference numerals in FIG. 4b. The automatic focus step (S15) of FIG. 4a, however, is bypassed altogether in the embodiment shown in FIG. 4b, and the process proceeds from step S14 directly to step S16. Also, where CPU 60 finds that none of the comparison scores calculated exceed the "upper threshold" in step S13, CPU 60 may perform an alignment check in accordance with the embodiment of FIG. 4b to verify that the reference measurement site cell 46 is in the best alignment with the measurement site cell currently under evaluation to compare the cells for similarities/dissimilarities. The alignment check may be performed using an internal software search or some external module.

In this embodiment, a searching routine known as a "spiral search," shown as steps S21 and S22, is performed a predetermined number of times, as tracked by spiral search limit counter (S22). The spiral search moves the image of the measurement site under scrutiny slightly in an attempt to locate a cell area which has a comparison score which exceeds the threshold in step S13. A typical "spiral search" which may be implemented in the invention is shown and described in U.S. Pat. No. 5,621,813, which is herein incorporated by reference in its entirety. Alternative search techniques, e.g., linear search, circular search, etc., may also be used in lieu of the spiral search (S21) technique described herein. Examples of such search techniques can be found in U.S. Pat. No. 5,487,172, which is also herein incorporated by reference in its entirety. If all of the comparison scores remain below the "upper threshold" value after a number of spiral search attempts are made, as tracked by spiral search counter in step S22, an error code is stored in measurement site memory 62 (S23) and the "live" image is captured and stored in the measurement site memory 62 (S24) before the process moves to a new measurement site (S10).

Figure 5A:
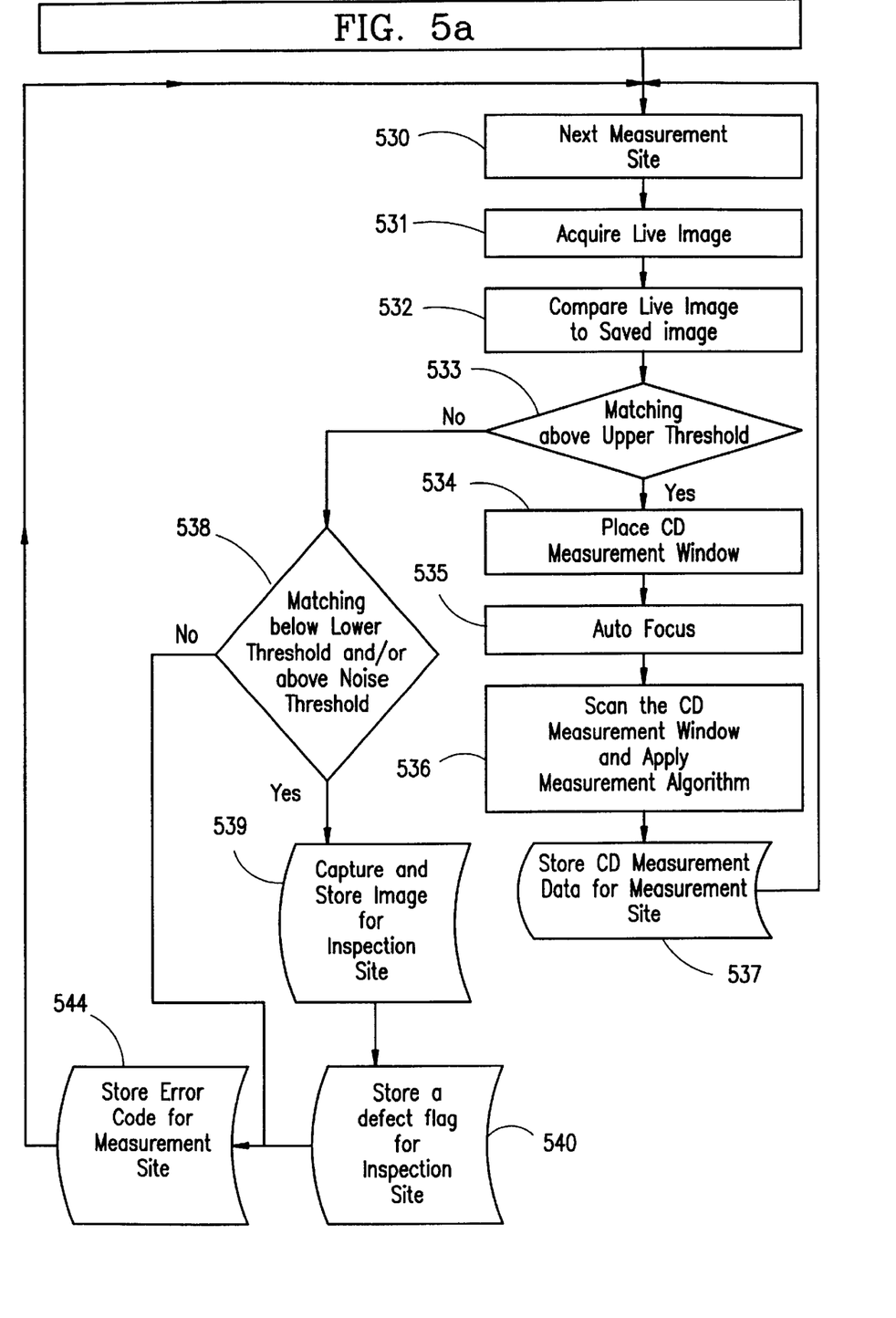
FIGS. 5a and 5b are flowcharts describing the operation of additional preferred embodiments of the invention.

In another preferred embodiment, a similar basic process flow chart is shown in FIG. 5a. Indeed, steps S30–S37 in FIG. 5a are identical to steps S10–S17 of FIG. 4a. However, instead of performing a pattern inspection routine after the CD measurements are made, as in steps S18, S19, and S20 shown in the embodiment of FIG. 4a, the same steps (shown in FIG. 5a as S38, S39 and S40) are now located after the step of determining that the comparison score does not exceed the "upper threshold" (S33). Also, the step of storing a defect flag in inspection memory (S40) shown in FIG. 5a does not proceed immediately to the next measurement site, as in FIG. 4a. Instead, in the embodiment of FIG. 5a, an error code for the measurement site is stored in measurement site memory 62 (S44), after which the process moves to the next measurement site (S20).

Figure 5B:
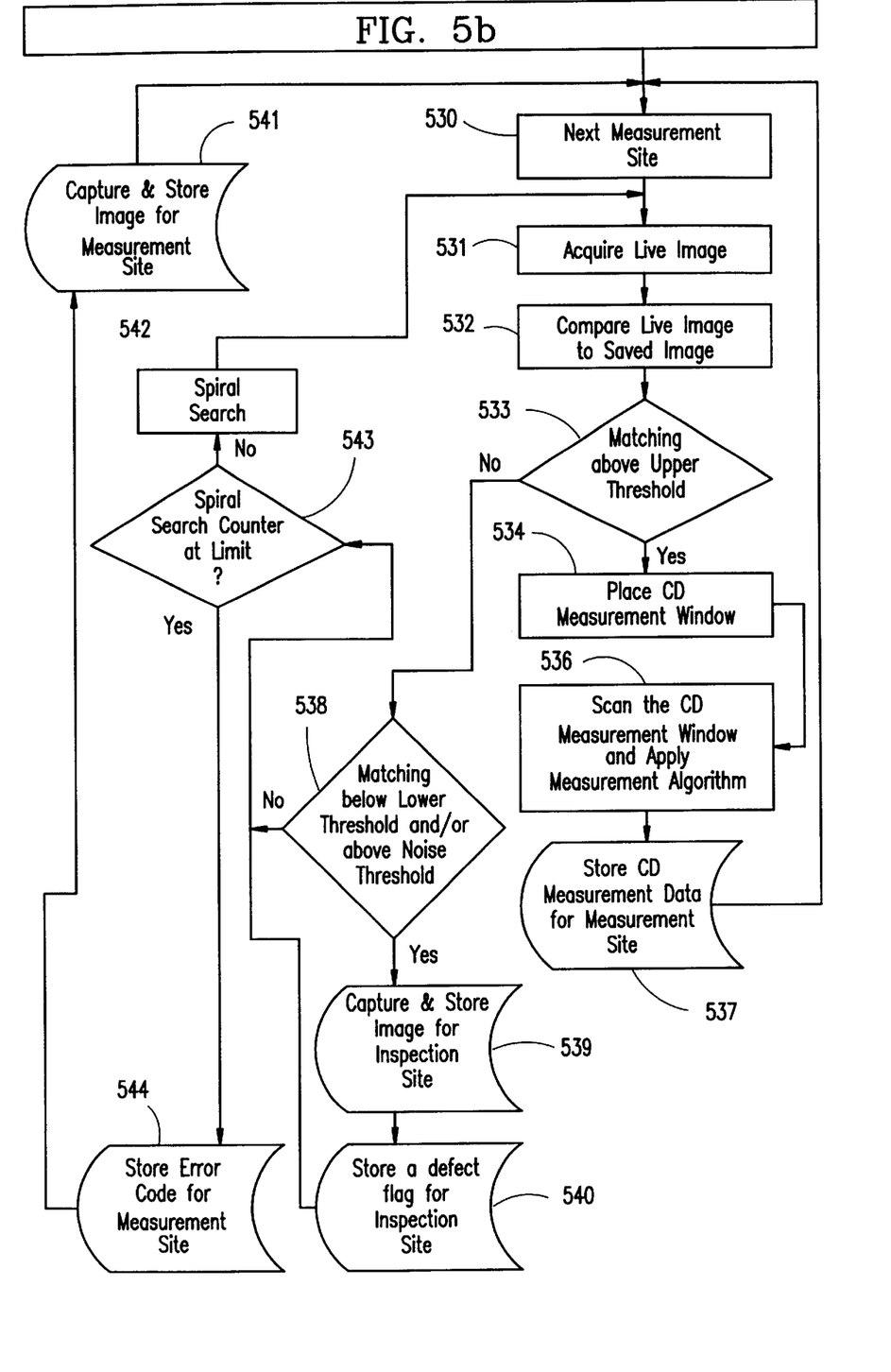

The embodiment shown in FIG. 5b is similar to that shown in FIG. 5a. The essential difference resides in the presence of an alignment check procedure, preferably in the form of a spiral search (S42, S43), in FIG. 5b, that can be made prior to storing an error code in the measurement site memory 62 (S44). The embodiment further includes the step (S41) of capturing and storing the image in measurement site memory 62 after the error code is stored.

In the embodiment of FIG. 6a, much of the same steps making up FIG. 5a, e.g., steps S30–S44, are identical to the steps used in FIG. 6a, e.g., steps S50–S67, respectively. The embodiment shown in FIG. 6a differs only by the addition of steps S58, S59 and S60. These steps follow the CD measurement procedures (steps S54 through S57). These added steps provide for an additional opportunity to perform pattern inspection using the same procedures found in steps S61, S62 and S63. Thus, the embodiment of FIG. 6a is a variation which combines the steps of both FIG. 4a and FIG. 5a to form another preferred embodiment of the invention.

Similarly, the embodiment of FIG. 6b is much like the embodiment of FIG. 5b in that steps S50 through S67 of FIG. 6b are identical to steps S30 through S44 of FIG. 5b. The embodiment of FIG. 6b, however, adds steps S58, S59 and S60, as described above.

The invention described herein provides a method and apparatus for detecting defects in an electronic device, such as an integrated circuit arrayed on a silicon wafer, while also scanning a surface area for CD measurement and without sacrificing throughput or processing speeds.

While the invention has been described in detail in connection with the best mode of the invention known at the time, it should be readily understood that the invention is not limited to any of the specified embodiments. Rather, the invention can be modified to incorporate any number of variations, alterations, substitutions or equivalent arrangements not heretofore described, which fall within the spirit and scope of the invention.

For example, any one or more of the modules 60–69 (FIG. 7) contained in computer 6 may be incorporated into one or more components (e.g., SEM 1, image processor 7, etc.) of the defect detection station (FIG. 2). Either local bus 69, main bus 70, or any connections to either bus may be replaced or supplemented by a remote local area network (LAN), intra/internet, or any other wired/wireless communication link that provides for communication between at least two points, as known in the art. The database 64 may be separated from computer 6 and connected by main bus 70 locally, or remotely through permanent or request-based (e.g., dial-up, etc.) communications links known in the art. The CD measure unit 63 (FIG. 7) may be any other type of measuring (or metrological device) known in the art for taking measurements of the dimensions or sizes of features, elements, components, etc. of an electronic device.

Regardless of the modifications later contemplated by those of ordinary skill in the art, the nature, spirit and scope of the invention is only limited by the scope of the claims appended hereto.

What is claimed as new and desired to be protected by Letters Patent of the United States is:

1. A testing device for use in detecting defects in the manufacture of an electronic device, the testing device comprising:
    a critical dimension measuring unit operative to scan and measure features of the electronic device at a measurement site which is indicative of a defect in the manufacture of the electronic device; and
    a pattern inspection unit operative to detect a pattern defect in the manufacture of the electronic device located at said measurement site, said pattern inspection unit utilizing images obtained during operation of said critical dimension measuring unit.

2. The testing device as in claim 1, wherein said critical dimension measuring unit includes a scanning electron-beam microscope.

3. A testing device as in claim 1, wherein said critical dimension measuring unit obtains a plurality of images of an electronic device as said critical dimension measuring unit scans said electronic device to find a proper location for performing a critical dimension measurement.

4. A testing device as in claim 3, wherein said critical dimension measuring unit compares a plurality of first images, each of which is at least a portion of one of said plurality of obtained images, with a reference image and provides an indication of a degree of similarity between the compared images.

5. A testing device as in claim 4, wherein said critical dimension measurement unit obtains a plurality of images from each of a plurality of measurement sites.

6. A testing device as in claim 4, wherein said critical dimension measuring unit stores each first image which is compared with said reference image together with an associated indication of the similarity of each first image to said reference image.

7. A testing device as in claim 6, wherein said pattern inspecting unit identifies as defective a pattern contained in any of said first images which has an associated similarity indication which is below a second similarity threshold.

8. A testing device as in claim 6, wherein said pattern inspecting unit identifies as defective a pattern contained in any of said first images which has an associated similarity indication which is below a second similarity threshold and above a noise threshold.

9. A testing device as in claim 6, wherein said pattern inspection unit is operative to perform a comparison between said reference pattern and a pattern within a first image, which first image has a similarity indication which is below a second similarity threshold.

10. A testing device as in claim 6, wherein said pattern inspection unit is operative to perform a comparison between said reference pattern and a pattern within a first image, which first image has a similarity indication which is below a second similarity threshold and above a noise threshold.

11. A testing device as in claim 6, wherein said critical dimension measuring unit performs critical dimension measurements on features contained within a first image which has an associated similarity indication which exceeds a first similarity threshold.

12. A testing device as in claim 11, wherein said critical dimension measuring unit places a critical dimension measuring window over a feature of said first image and scans said image to the extent defined by said window, and executes a measurement algorithm to obtain critical dimension measurement data.

13. A testing device as in claim 12, wherein said critical dimension measurement unit stores said critical dimension measurement data together with data identifying the site of the critical dimension measurement.

14. A testing device as in claim 12, wherein said pattern inspection unit is operative after said critical dimension measurement unit obtains said critical dimension measurement data.

15. A testing device as in claim 11, wherein said critical dimension measuring unit indicates an error for said measurement site if none of said first images has an associated similarity indication which exceeds said first similarity threshold.

16. A testing device as in claim 11, wherein said first similarity threshold is preset by an operator.

17. A testing device as in claim 11, wherein said critical dimension measuring unit evaluates the similarity indications of all said first images and sets said first similarity threshold based on said evaluation.

18. A testing device as in claim 17, wherein said critical dimension measuring unit sets said first similarity threshold so that only a first image having the highest similarity indication exceeds said first similarity threshold.

19. A testing device as in claim 11, wherein said critical dimension measuring unit conducts a procedure to rescan said electronic device at a location near said measurement site in an attempt to obtain a plurality of images from which a first image which has a similarity indication which exceeds said first similarity threshold can be obtained.

20. A testing device as in claim 19, wherein said critical dimension measuring unit conducts said procedure a predetermined number of times and if a first image which has a similarity indication which exceeds said first similarity threshold still cannot be obtained an error is indicated for said measurement site.

21. A testing device as in claim 19, wherein said critical dimension measuring unit conducts said procedure a predetermined number of times and if a first image which has a similarity indication which exceeds said first similarity threshold still cannot be obtained, and if a first image which has a similarity indication which falls below a second threshold cannot be obtained, an error is indicated for said measurement site.

22. A testing device as in claim 11, wherein if none of said first images has an associated similarity indication which exceeds said first similarity threshold, said pattern inspection unit examines said first images to determine if any of said first images has a similarity indication which is below a second similarity threshold.

23. A testing device as in claim 22, wherein if none of said first images has a similarity indication which is below a second similarity threshold, said critical dimension measuring unit stores an error indication for the measurement site.

24. A testing device as in claim 22, wherein if a said first image has a similarity indication which is below said second similarity threshold, it is identified as representing a defective pattern.

25. A testing device as in claim 22, wherein if none of said first images has a similarity indication which is below a second similarity threshold, said critical dimension measuring unit conducts a procedure to rescan said electronic device at a location near said measurement site in an attempt to obtain a plurality of images from which a first image which has a similarity indication which exceeds said first similarity threshold can be obtained.

26. An inspection station subsystem comprising:
   a microscope which illuminates an object and generates an image corresponding to the object;
   an image analyzer, which receives the image generated by said microscope, said image analyzer formulating a similarity value based on similarities between the image and a reference image;
   a comparing unit which compares the similarity value with first and second reference values;
   a critical dimension measuring unit for performing a critical dimension measurement on the image when said comparing unit indicates that the similarity value exceeds the first reference value; and
   a pattern inspection unit which performs a defect detection on the image when said comparing unit indicates that the similarity value is below the second reference value.

27. The inspection station subsystem of claim 26, wherein the object is a semiconductor device having a pattern where a critical dimension measurement is to be made.

28. The inspection station subsystem of claim 27, wherein the object is a semiconductor device having a pattern, the image representing said pattern, said pattern inspection unit detecting a defect in the semiconductor device when the image does not substantially match a reference pattern.

29. The inspection station subsystem of claim 26, further comprising:
   a threshold signal generator, responsive to said comparing unit, for generating a measurement signal for initiating a critical dimension measurement when the similarity value exceeds the first reference value; and
   said critical dimension measuring unit measuring a critical dimension of at least one element of the object in response to said measurement signal.

30. The inspection station subsystem of claim 29, wherein said object is a semiconductor device and said critical dimension measuring unit measures a critical dimension of said semiconductor device.

31. A system for measuring the size of one of a plurality of features of an integrated circuit fabricated on a semiconductor wafer, wherein respective ones of the plurality of features appear at different locations on the semiconductor wafer, the system comprising:
   an electron microscope for forming an image of an area on the semiconductor wafer;
   a controller for causing said microscope to examine and create images for different areas on the semiconductor wafer;
   a storage unit for storing a reference image;
   a size measuring device for measuring, in response to a first enabling signal, the size of at least one of the features of the semiconductor wafer located within an image area of said microscope;
   a pattern detector for detecting, in response to a second enabling signal, a defect in a pattern contained within an image area of said microscope;
   a first comparator for comparing at least a portion of an area imaged by said microscope with said reference image and for generating respective similarity values for each area portion;
   a second comparator for comparing the similarity value of each of said area portions with a first threshold and generating said first enabling signal when said first threshold is exceeded;
   a third comparator for comparing the similarity values of each of said area portions with a second threshold and generating said second enabling signal when said similarity value is below said second threshold.

32. The measuring system as in claim 31, wherein said first, second and third comparators are operative such that said first enabling signal is generated when said microscope is focused on a feature location having the most similarities, and said second enabling signal is generated when said microscope is focused on the feature location having the least similarities.

33. The measuring system as in claim 31, wherein said electron microscope is a scanning electron-beam microscope for scanning different locations on a single integrated circuit.

34. A critical dimension (CD) measurement apparatus for measuring critical dimensions of integrated circuit (IC) features during fabrication of semiconductor ICs on a silicon wafer, the measurement apparatus comprising:
   a scanning electron-beam microscope (SEM) having at least:
      a moveable stage supporting a silicon wafer during fabrication;
      an electron beam gun, operatively coupled to said moveable stage, which emits a beam of electrons towards the silicon wafer;
      a beam deflector, operatively coupled to said electron beam gun, which receives the emitted beam of electrons and directs the emitted beam of electrons across a portion of a surface of the silicon wafer covering a measurement site on the surface of the silicon wafer; and
      a serial detector, operatively coupled to said moveable stage, wherein said serial detector operates to detect secondary electrons emitted from the silicon wafer, and to output a detection signal representative of the secondary electrons detected;
   wherein, the CD measurement apparatus further comprises:

an image processor, operatively coupled to said serial detector, receiving the detection signal output by said serial detector, wherein said image processor generates a live image signal of the measurement site in response to the detection signal output by said serial detector;

an image memory, operatively coupled to said image processor, said image memory storing the live image generated by said image processor;

a display device, coupled to said image processor, which displays the live image stored in said image memory; and a SEM computer having at least:
a central processing unit, operatively coupled to said image processor, wherein said central processing unit compares at least a portion of the live image in said image memory to a stored reference image and calculates a plurality of comparison scores based on similarities between respective portions of said live image and the stored reference image, wherein said central processing unit generates a measurement signal when at least one comparison score exceeds an upper threshold score, and generates an inspection signal when at least one comparison score is below a lower threshold score;

a critical dimension measurement unit, operatively coupled to said central processing unit, responsive to the measurement signal generated by said central processing unit to make CD measurements of features on the surface of the silicon wafer based on the detection signals output by said serial detector to determine presence of CD measurement defects in the silicon wafer;

a pattern inspection unit, operatively coupled to said central processing unit, responsive to the inspection signal generated by said central processing unit to inspect patterns corresponding to features on the surface of the silicon wafer based on the detection signal output by said serial detector, wherein said pattern inspection unit compares the inspection patterns from the surface of the silicon wafer to reference patterns stored in the database to determine presence of pattern defects in the silicon wafer; and a SEM control unit, operatively coupled to said central processing unit, wherein said SEM control unit controls the moveable stage of said SEM to permit said SEM access to a plurality of measurement sites on the silicon wafer.

35. A method of detecting defects in the manufacture of an electronic device, the method comprising the steps of:
scanning a measurement site of the electronic device to produce a plurality of images associated with said measurement site;
comparing each of said images with a reference pattern and providing an indication of a degree of similarity of each of said images to said reference pattern;
performing a critical dimension measurement on an image which has a degree of similarity which exceeds a first threshold; and
performing a defect detection-operation on an image which has a degree of similarity which is below a second threshold.

36. The method as in claim 35, wherein said critical dimension measurement comprises the steps of:
performing a critical dimension measurement on predetermined features of said electronic device contained within said image which has a degree of similarity which exceeds said first threshold.

37. The method as in claim 35, wherein said defect detection operation comprising the steps of:
identifying the image which has a degree of similarity which is below said second threshold as representing a defective area of said electronic device.

38. The method as in claim 37, wherein the electronic device is a silicon wafer having a plurality of semiconductor integrated circuits, and wherein said comparing step includes a comparison between an image of a circuit element of one integrated circuit fabricated in the silicon wafer and a reference image of a corresponding circuit element from another integrated circuit.

39. A method of evaluating a semiconductor device, the method comprising the steps of:
scanning a plurality of locations of the semiconductor device;
outputting a plurality of image signals respectively corresponding to ones of the plurality of locations;
comparing each of the plurality of image signals with a stored reference image signal, and noting similarities relative to the stored reference image signal;
selecting one of the plurality of locations associated with the smallest number of similarities noted relative to the stored reference image signal;
storing a pattern error flag corresponding to the selected one of the plurality of locations on the semiconductor device;
determining which one of the plurality of locations is associated with the highest number of similarities relative to the stored reference image signal; and
measuring dimensions of the semiconductor device at the location determined in said determining step.

40. The method as in claim 39, wherein said step of scanning is performed using an optical microscope.

41. In a semiconductor integrated circuit manufacturing system, a critical dimension measurement (CD) process comprising the steps of:
scanning a surface of a semiconductor wafer and defining a measurement site on the surface of the semiconductor wafer;
generating an image signal associated with a topology of the semiconductor wafer at the measurement site;
storing an image of the measurement site;
comparing the stored image to a reference image and calculating a plurality of similarity scores based on similarities between portions of the stored image and the reference image; and
determining whether any of the comparison scores exceeds a first threshold score, wherein said determining step includes the step of performing an additional scan of the surface of said semi conductor wafer when none of the comparison scores exceeds the first threshold score,
performing a measurement process on an associated portion of the stored image when one of the comparison scores exceeds the first threshold score;
determining whether any of the comparison scores is below a second threshold score, and, when a comparison score is below the second threshold score, storing a defect indication in association with the portion of said stored image which has the comparison score below the second threshold score.

42. A critical dimension measurement process for measuring critical dimensions of integrated circuit (IC) features on a silicon wafer, the measurement process comprising the steps of:
  placing a silicon wafer on a moveable stage;
  emitting a beam of electrons;
  scanning a surface of the silicon wafer by deflecting the beam of electrons obtained from said emitting step across a portion of the surface of the silicon wafer to define a first measurement site on the surface of the silicon wafer;
  serially detecting secondary electrons emitted from the silicon wafer as a result of said scanning step;
  storing in an image memory a live image of the measurement site of the surface of the silicon wafer corresponding to the secondary electrons detected in said serially detecting step;
  comparing portions of the live image in the image memory to a stored reference image and calculating a plurality of comparison scores corresponding to said portions based on similarities between the portions of said live image and the stored reference image; and
  determining whether at least one comparison score exceeds a predetermined upper threshold score, wherein said determining step includes the step of performing search and scanning process around said first measurement site when no comparison score exceeds the predetermined upper threshold score, and the step of performing a measurement process when at least one comparison score does exceed the predetermined upper threshold score;
  wherein said additional search and scanning process includes the substep of:
    storing an error code in a measurement site memory, and moving the stage to permit scanning of another measurement site in the vicinity of said first measurement site;
  wherein said measurement process includes the substeps of:
    determining placement of a critical dimension (CD) measurement window;
    scanning the CD measurement window;
    performing CD measurements on CD features on the surface of the silicon wafer within the CD measurement window;
    storing measurement data resulting from performance of said performing CD measurements substep in the measurement site memory;
    determining if any comparison scores fall below a predetermined lower threshold score; and
    where any comparison score falls below the predetermined lower threshold score, capturing the portion of the live image having the comparison score below the predetermined lower threshold score and storing that portion of the live image, together with a defect flag in an inspection site memory.

43. The critical dimension measurement process as in claim 42,
  wherein said additional search process further includes the substep of:
    prior to said substep of storing an error code, retrieving a search count and determining whether said search count has exceeded a predetermined limit; and
    where the count limit has not been exceeded, performing a search, incrementing the search count, and permitting additional scanning of said another measurement site;
  wherein said substep of storing an error code further includes the substep of capturing and storing the live image in the measurement site memory.

44. The critical dimension measurement process as in claim 43, wherein said measurement process further includes the substeps of:
  where no comparison score falls below the predetermined lower threshold score, capturing the live image and storing the live image in the measurement site memory.

45. A critical dimension measurement process for measuring critical dimensions of integrated circuit (IC) features during fabrication of semiconductor ICs on a silicon wafer, the measurement process comprising the steps of:
  placing a silicon wafer on a moveable stage;
  emitting a beam of electrons;
  scanning a portion of the surface of the silicon wafer with a beam of electrons, said surface portion defining a measurement site;
  serially detecting secondary electrons emitted from the silicon wafer as a result of said scanning step, thereby forming a live image of said measurement site;
  storing said live image of the measurement site in an image memory;
  comparing portions of said live image stored in the image memory with a stored reference image and calculating a plurality of comparison scores based on similarities between each compared portion of the live image and the stored reference image; and
  determining whether at least one comparison score exceeds a predetermined upper threshold score, wherein said determining step includes the step of performing search and scanning process when no comparison score exceeds the predetermined upper threshold score, and the step of performing a measurement process when any comparison score does exceed the predetermined upper threshold score;
  wherein said additional search and scanning process includes the substeps of:
    evaluating whether any comparison score falls below a predetermined lower threshold score;
    where at least one comparison score does fall below the predetermined lower threshold score, capturing the live image and storing the live image, together with a defect flag in an inspection site memory, and storing an error code in a measurement site memory, and moving the stage to permit scanning of another measurement site;
  wherein said measurement process includes the substeps of:
    determining placement of a critical dimension (CD) measurement window;
    scanning the CD measurement window;
    performing CD measurements on CD features on the surface of the silicon wafer within the CD measurement window; and
    storing measurement data resulting from said performing CD measurements substep in the measurement site memory.

46. The critical dimension measurement process of claim 45,
  wherein said additional search process further includes the substeps of:
    where no comparison score falls below the predetermined lower threshold score, storing an error code in a measurement site memory, and moving the stage to permit scanning of another measurement site.

47. The critical dimension measurement process of claim 45,
  wherein said additional search process further includes the substep of:
    where no comparison score falls below the predetermined lower threshold score, retrieving a search count and determining whether a count limit has been reached;
    where the count limit has not been reached, performing a search, incrementing the search count, and conducting additional scanning around the measurement site in said scanning step; and
    upon determining that the count limit has been reached, storing an error code and the live image in the measurement site memory.

48. The critical dimension measurement process of claim 47,
  wherein said additional search process further includes the substep of:
    after the error code is stored upon determining that the count limit had been reached, capturing and storing the live image in the measurement site memory.

* * * * *

UNITED STATES PATENT AND TRADEMARK OFFICE
CERTIFICATE OF CORRECTION

PATENT NO. : 6,452,677 B1
DATED : September 17, 2002
INVENTOR(S) : Douglas D. Do et al.

It is certified that error appears in the above-identified patent and that said Letters Patent is hereby corrected as shown below:

Column 4,
Line 47, "while-" should read -- while --
Line 48, "merry" should read -- memory --

Signed and Sealed this

Twenty-eighth Day of January, 2003

JAMES E. ROGAN
*Director of the United States Patent and Trademark Office*